(12) United States Patent
Germansen et al.

(10) Patent No.: US 7,655,766 B2
(45) Date of Patent: Feb. 2, 2010

(54) COMPOSITIONS COMPRISING POSITIONAL ISOMERS OF PEGYLATED G-CSF

(76) Inventors: Carsten Germansen, Juni Alle 168, Herlev (DK) 2730; Bobby Soni, Caroline Amalievej 58B, Kgs Lyngby (DK) 2800; Grethe Rasmussen, Brudedalen 1, Farum (DK) 3520

( * ) Notice: Subject to any disclaimer, the term of this patent is extended or adjusted under 35 U.S.C. 154(b) by 97 days.

(21) Appl. No.: 11/742,445

(22) Filed: Apr. 30, 2007

(65) Prior Publication Data

US 2008/0090764 A1 Apr. 17, 2008

Related U.S. Application Data

(62) Division of application No. 11/420,546, filed on May 26, 2006, now Pat. No. 7,381,805.

(60) Provisional application No. 60/686,726, filed on Jun. 1, 2005.

(51) Int. Cl.
C07K 14/53 (2006.01)
A61K 47/36 (2006.01)
A61K 38/24 (2006.01)

(52) U.S. Cl. .................... 530/402; 530/350; 530/351; 530/395; 530/399; 514/2; 514/8; 424/198.1; 435/69.5

(58) Field of Classification Search .................. None
See application file for complete search history.

(56) References Cited

U.S. PATENT DOCUMENTS

| | | | |
|---|---|---|---|
| 4,810,643 A | 3/1989 | Souza | |
| 4,833,127 A | 5/1989 | Ono et al. | |
| 4,853,871 A | 8/1989 | Pantoliano et al. | |
| 4,904,584 A | 2/1990 | Shaw | |
| 4,908,773 A | 3/1990 | Pantoliano et al. | |
| 4,999,291 A | 3/1991 | Souza | |
| 5,023,802 A | 6/1991 | Fujita | |
| 5,025,388 A | 6/1991 | Cramer et al. | |
| 5,104,651 A | 4/1992 | Boone | |
| 5,109,119 A | 4/1992 | Reichert et al. | |
| 5,157,736 A | 10/1992 | Boyer et al. | |
| 5,214,132 A | 5/1993 | Kuga et al. | |
| 5,218,092 A | 6/1993 | Sasaki et al. | |
| 5,265,030 A | 11/1993 | Skolnick et al. | |
| 5,281,698 A | 1/1994 | Nitecki | |
| 5,307,287 A | 4/1994 | Cramer et al. | |
| 5,320,840 A | 6/1994 | Camble et al. | |
| 5,349,052 A | 9/1994 | Delgado et al. | |
| 5,362,853 A | 11/1994 | Kuga et al. | |
| 5,386,507 A | 1/1995 | Teig et al. | |
| 5,399,345 A | 3/1995 | Schumacher et al. | |
| 5,416,195 A | 5/1995 | Camble et al. | |
| 5,424,963 A | 6/1995 | Turner et al. | |
| 5,448,498 A | 9/1995 | Namiki et al. | |
| 5,476,653 A | 12/1995 | Pitt et al. | |
| 5,555,366 A | 9/1996 | Teig et al. | |
| 5,580,755 A | 12/1996 | Souza | |
| 5,581,476 A | 12/1996 | Osslund | |
| 5,582,823 A | 12/1996 | Souza | |
| 5,589,456 A | 12/1996 | Smith et al. | |
| 5,597,562 A | 1/1997 | Nomura et al. | |
| 5,676,941 A | 10/1997 | Souza | |
| 5,681,720 A | 10/1997 | Kuga et al. | |
| 5,738,849 A | 4/1998 | Bauer et al. | |
| 5,772,992 A | 6/1998 | Bauer et al. | |
| 5,773,581 A | 6/1998 | Camble et al. | |
| 5,790,421 A | 8/1998 | Osslund | |
| 5,795,968 A | 8/1998 | Kuga et al. | |
| 5,817,486 A | 10/1998 | Bauer et al. | |
| 5,824,778 A | 10/1998 | Ishikawa et al. | |
| 5,824,784 A | 10/1998 | Kinstler et al. | |
| 5,830,705 A | 11/1998 | Souza | |
| 5,858,347 A | 1/1999 | Bauer et al. | |
| 5,880,255 A | 3/1999 | Delgado et al. | |
| 5,883,230 A | 3/1999 | Schendel | |
| 5,985,263 A | 11/1999 | Lee et al. | |
| 5,985,265 A | 11/1999 | Kinstler et al. | |
| 5,997,860 A | 12/1999 | Bauer et al. | |
| 6,004,548 A | 12/1999 | Souza | |
| 6,017,523 A | 1/2000 | Bauer et al. | |
| 6,022,535 A | 2/2000 | Bauer et al. | |
| 6,027,720 A | 2/2000 | Kuga et al. | |
| 6,030,812 A | 2/2000 | Bauer et al. | |
| 6,051,217 A | 4/2000 | Bauer et al. | |

(Continued)

FOREIGN PATENT DOCUMENTS

AU 631312 B 11/1992

(Continued)

OTHER PUBLICATIONS

Aritomi et al., Atomic structure of the GCSF-receptor complex showing a new cytokine-receptor recognition scheme. Nature 401:713-717 (1999).

(Continued)

Primary Examiner—Christine J Saoud
Assistant Examiner—Elly-Gerald Stoica
(74) Attorney, Agent, or Firm—Joanne R. Petithory; Norman J Kruse; Maxygen, Inc.

(57) ABSTRACT

A method for increasing the stability and uniformity of a PEGylated G-CSF polypeptide having at least one PEG moiety attached to the epsilon amino group of a lysine residue or the N-terminal amino group and at least one PEG moiety attached to a hydroxyl group, comprising subjecting the polypeptide to an elevated pH of above 8.0 for a period of time suitable to remove PEG moieties attached to a hydroxyl group, and reducing the pH to about 8.0 or lower; as well as PEGylated G-CSF polypeptides and compositions produced according to the method and methods for increasing neutrophil levels in a patient using the PEGylated G-CSF polypeptides and compositions.

6 Claims, 4 Drawing Sheets

U.S. PATENT DOCUMENTS

| | | | |
|---|---|---|---|
| 6,057,133 | A | 5/2000 | Bauer et al. |
| 6,060,047 | A | 5/2000 | Bauer et al. |
| 6,066,318 | A | 5/2000 | Feng et al. |
| 6,074,639 | A | 6/2000 | Bauer et al. |
| 6,093,395 | A | 7/2000 | Bauer et al. |
| 6,100,070 | A | 8/2000 | Zurfluh et al. |
| 6,132,991 | A | 10/2000 | Bauer et al. |
| 6,153,183 | A | 11/2000 | Bauer et al. |
| 6,166,183 | A | 12/2000 | Ishikawa et al. |
| 6,204,364 | B1 | 3/2001 | Todaro et al. |
| 6,261,550 | B1 | 7/2001 | Osslund |
| 6,379,661 | B1 | 4/2002 | Souza |
| 6,420,339 | B1 | 7/2002 | Gegg |
| 6,555,660 | B2 | 4/2003 | Nissen et al. |
| 6,632,426 | B2 | 10/2003 | Osslund |
| 6,646,110 | B2 | 11/2003 | Nissen et al. |
| 6,831,158 | B2 | 12/2004 | Nissen et al. |
| 7,381,804 | B2 | 6/2008 | Osslund |
| 7,381,805 | B2 | 6/2008 | Germansen et al. |
| 2002/0142964 | A1 | 10/2002 | Nissen et al. |
| 2003/0158375 | A1 | 8/2003 | Nissen et al. |
| 2003/0171559 | A1 | 9/2003 | Osslund |
| 2003/0204057 | A1 | 10/2003 | Ishikawa et al. |
| 2005/0095684 | A1 | 5/2005 | Nissen et al. |
| 2005/0147587 | A1 | 7/2005 | Nissen et al. |
| 2006/0084793 | A1 | 4/2006 | Nissen et al. |

FOREIGN PATENT DOCUMENTS

| | | |
|---|---|---|
| AU | 641081 B | 9/1993 |
| EP | 0243153 A2 | 10/1987 |
| EP | 0 256 843 A1 | 2/1988 |
| EP | 0272703 A1 | 6/1988 |
| EP | 0 335 423 A2 | 10/1989 |
| EP | 0 215 126 B1 | 7/1991 |
| EP | 0 220 520 B1 | 9/1991 |
| EP | 0459630 A2 | 12/1991 |
| EP | 0473268 A2 | 3/1992 |
| EP | 0490584 A2 | 6/1992 |
| EP | 0 344 796 B1 | 9/1994 |
| EP | 0 230 980 B2 | 3/1996 |
| EP | 0 401 384 B1 | 3/1996 |
| EP | 0 744 409 A1 | 11/1996 |
| EP | 0 370 205 B1 | 7/1998 |
| EP | 0 733 067 B1 | 5/1999 |
| EP | 0 921 131 A1 | 6/1999 |
| EP | 0 237 545 B2 | 8/1999 |
| EP | 0 169 566 B2 | 7/2000 |
| EP | 0 612 846 B1 | 8/2000 |
| EP | 1 167 390 A1 | 1/2002 |
| GB | 2213821 A | 8/1989 |
| WO | 85/00817 A1 | 2/1985 |
| WO | 88/01775 A1 | 3/1988 |
| WO | 89/05824 A1 | 6/1989 |
| WO | 89/10932 A1 | 11/1989 |
| WO | 90/12874 A2 | 11/1990 |
| WO | 91/05798 A1 | 5/1991 |
| WO | 92/04455 A1 | 3/1992 |
| WO | 9221029 A1 | 11/1992 |
| WO | 93/25687 A1 | 12/1993 |
| WO | 94/20069 A1 | 9/1994 |
| WO | 95/20976 A1 | 8/1995 |
| WO | 95/20977 A1 | 8/1995 |
| WO | 95/21197 A1 | 8/1995 |
| WO | 95/21254 A1 | 8/1995 |
| WO | 95/21629 A1 | 8/1995 |
| WO | 95/27732 A2 | 10/1995 |
| WO | 87/01132 A1 | 2/1996 |
| WO | 96/11953 A1 | 4/1996 |
| WO | 96/23888 A1 | 8/1996 |
| WO | 97/12977 A1 | 4/1997 |
| WO | 97/12978 A1 | 4/1997 |
| WO | 97/12985 A2 | 4/1997 |
| WO | WO9711957 | 4/1997 |
| WO | 98/17810 A2 | 4/1998 |
| WO | 98/18923 A1 | 5/1998 |
| WO | 98/18924 A1 | 5/1998 |
| WO | 98/46750 A1 | 10/1998 |
| WO | 98/53072 A1 | 11/1998 |
| WO | 99/03887 A1 | 1/1999 |
| WO | 99/67291 A2 | 12/1999 |
| WO | 00/18905 A1 | 4/2000 |
| WO | 00/40728 A1 | 7/2000 |
| WO | 00/44785 A1 | 8/2000 |
| WO | 00/52057 A1 | 9/2000 |
| WO | 01/04329 A1 | 1/2001 |
| WO | 01/51510 A2 | 7/2001 |
| WO | 02/20751 A2 | 3/2002 |
| WO | 02/20766 A2 | 3/2002 |
| WO | 02/28896 A1 | 4/2002 |
| WO | 02/36626 A1 | 5/2002 |
| WO | 03/006501 A2 | 1/2003 |

OTHER PUBLICATIONS

Bazan JF, Haemopoietic receptors and helical cytokines. Immunology Today 1990; 11(10) 350-354.

Bowen et al., Relationship between molecular mass and duration of activity of polyethylene glycol conjugated granulocyte colony-stimulating factor mutein. Experimental Hematology 27: 425-432 (1999).

Bowie Ju, et al. Deciphering the message in protein sequences: tolerance to amino acid substitutions. Science 1990; 247(4948):1306-1310.

De Haan, G., et al., Efficient mobilization of haematopoietic progenitors after a single injection of pegylated recombinant human granulocyte colony-stimulating factor in mouse strains with distinct marrow-cell pool sizes. British Journal of Haematology (2000) 110(3):638-646.

Delgado, C, et al., The Uses and Properties of PEG-Linked Proteins. Critical Reviews in Therapeutic Drug Carrier Systems 9 (3, 4): 249-304 (1992).

Eliason J.F., et al. Extended activity in cynomolgus monkeys of a granulocyte colony-stimulating factor mutein conjugated with high molecular weight polyethylene glycol. Stem Cells, Jan. 2000, vol. 18, No. 1, 40-45.

Gervais V, et al. NMR investigations of the role of the sugar moiety in glycosylated recombinant human granulocyte-colony-stimulating factor. Eur J Biochem. 1997; 247(1):386-395.

Hershfield MS, et al. Use of site-directed mutagenesis to enhance the epitope-shielding effect of covalent modification of proteins with polyethylene glycol. Proc Natl Acad Sci USA. 1991; 88(16):7185-7189.

Hill et al., The structure of granulocyte-colony-stimulating factor and its relationship to other growth factors. Proc. Natl. Acad. Sci. USA 90: 5167-5171 (1993).

Horan et al., Dimerization of the extracellular domain of granuloycte-colony stimulating factor receptor by ligand binding: a monovalent ligand induces 2:2 complexes. Biochemistry 35(15): 4886-4896 (1996).

Li, T. et al., Conformational Changes in G-CSF/Receptor Complex as Investigated by Isotope-Edited FTIR. Spectroscopy. Biochemistry 1997; 36(29):8849-8857.

Nagata et al., Molecular cloning and expression of cDNA for human granulocyte colony-stimulating factor. Nature 319:415-418 (1986).

Osslund, T. The Structure of Granulocyte-Colony Stimulating Factor. Ph.D. Thesis, University of California Los Angeles 1993.

Reidhaar-Olson et al., Identification of residues critical to the activity of human granulocyte colony stimulating factor. Biochemistry 35: 9034-9041 (1996).

Satake-Ishikawa et al., Chemical modification of recombinant human granulocyte colony-stimulating factor by polyethylene glycol increases its biological activity in vivo. Cell Structure and Function 17:157-160 (1992).

Souza et al., Recombinant human granulocyte colony-stimulating factor: effects on normal and leukemic myeloid cells. Science 232: 61-65 (1986).

Viens, P., et al., Randomized, Controlled, Dose-Range Study of Ro 25/8315 Given Before and After a High-Dose Combination Chemotherapy Regimen in Patients with Metastatic or Recurrent Breast Cancer Patients, J. Clinical Oncology, 20(1):24-36 (2002).

Yamasaki, M., et al., Effect of Divalent Polyethylene Glycol Units, Conjugated on Human Granulocyte Colony-Stimulating Factor, on Biological Activities In Vitro and In Vivo. Drugs Exptl. Clin. Res. 24(4):191-196 (1998).

Young, D.C. et al., Characterization of the receptor binding determinants of granulocyte colony stimulating factor. Protein Science (1997), 6:1228-1236.

Zink T. et al. Secondary structure of human granulocyte-colony stimulating factor derived from NMR spectroscopy. FEBS Letters 314(3) 435-439 (1992).

Zink T. et al., Structure and dynamics of the human granulocyte colony-stimulating factor determined by NMR spectroscopy. Loop mobility in a four-helix-bundle protein. Biochemistry 33: 8453-8463 (1994).

Zurawski, S.M. et al. Definition and spatial location of mouse interleukin-2 residues that interact with its heterotrimeric receptor EMBO J. 1993; 12:5113-19.

Abdel-Meguid et al., Three-dimensional structure of a genetically engineered variant of porcine growth hormone. PNAS 84:6434-6437 (1987).

Abrahmsen L, et al. Engineering subtilisin and its substrates for efficient ligation of peptide bonds in aqueous solution. Biochemistry 30(17):4151-4159 (1991).

Carter et al, Protein crystallization using incomplete factorial experiments. J. Biol. Chem. 254:12219-12223 (1979).

Carter et al., Statistical design of experiments for protein crystal growth. J. Cryst. Growth 90: 60-73 (1988).

Cox et al., Experiments with automated protein crystallization. J. Appl. Crystallogr. 20: 366-373 (1987).

Cox et al., An investigation of protein crystallization parameters. J. Cryst. Growth 90: 318-324 (1988).

Cunningham et al., High-resolution epitope mapping of hGH-receptor interactions by alanine-scanning mutagenesis. Science 244:1081-1084 (1989).

De Vos et al., Human growth hormone and extracellular domain of its receptor: crystal structure of the complex. Science 255: 305-312 (1992).

Diederichs et al., Novel fold and putative receptor binding site of granulocyte-macrophage colony-stimulating factor. Science 254:1779-1782 (1991).

Feng et al., Circular permutation of granulocyte colony-stimulating factor. Biochemistry 38(14):4553-4563 (1999).

Gabrilove, J. Introduction and overview of hematopoietic growth factors. Seminars in Hematology 26:(2, Suppl 2) 1-14 (1989).

Huse et al., Generation of a large combinatorial library of the immunoglobulin repertoire in phage lambda. Science 246:1275-1281 (1989).

Ishikawa et al., The substitution of cysteine 17 of recombinant human G-CSF with alanine greatly enhanced its stability. Cell Structure and Function, 17: 61-65 (1992).

Jancarik et al., Sparse matrix sampling: a screening method for crystallization of proteins. J. Appl. Crystallogr. 24: 409 (1991).

Jones et al., Growth factors in haemopoiesis. Bailliere's Clinical Hematology 2 (1): 83-111 (1989).

Kuga et al., Mutagenesis of human granulocyte colony stimulating factor. Biochem. Biophy. Res. Comm 159:103-111 (1989).

Layton et al., Identification of a functional domain of human granulocyte colony-stimulating factor using neutralizing monoclonal antibodies. JBC 266: 23815-23823 (1991).

Layton et al., Interaction of G-CSF with its receptor: dissociation of biological activity and receptor binding. J. of Cell. Biochem. Suppl. 17B:78, Abstract E225 (1993).

Li, et al., Structure-function analysis of the C-terminal segment of human interleukin-6. J. Biol. Chem. 268(30) 22377-22384 (1993).

Lieshke et al., Granulocyte colony-stimulating factor and granulocyte macrophage colony-stimulating factor (Parts 1 and 2). N. Engl. J. Med. 327: 28-34 and 99-106 (1992).

Lovejoy et al., Crystal structure of canine and bovine granulocyte-colony stimulating factor (G-CSF). J. Mol. Biol. 234:640-653 (1993).

Lu et al., Disulfide and secondary structures of recombinant human granulocyte colony stimulating factor. Arch. Biochem. Biophys. 268: 81-92 (1989).

Mckay, D.B. Response to technical comment. Science 257:412-413 (1992).

McWherter et al., Circular permutation of the granulocyte colony-stimulating factor receptor agonist domain of myelopoietin. Biochemistry 38 (14): 4564-4571 (1999).

Moore et al., Synergy of interleukin 1 and granulocyte colony-stimulating factor: in vivo stimulation of stem-cell recovery and hematopoietic regeneration following 5-fluorouracil treatment of mice. Proc. Natl. Acad. Sci. USA 84:7134-7138 (1987).

Nagata et al., The chromosomal gene structure and two mRNAs for human granulocyte colony-stimulating factor. EMBO J. 5: 575-581 (1986).

Nagahara et al., Crystallization and preliminary diffraction studies of recombinant human granulocyte-stimulating factor (KW2228). J. Mol. Biol. 214: 25-26 (1990).

Nicola et al., Separation of functionally distinct granulocyte-macrophage colony-stimulating factors. Blood 54: 614-627 (1979).

Nicola, N.A. Hematopoietic cell growth factors and their receptors. Annu. Rev. Biochem. 58: 45-77 (1989).

Pandit et al., Three-dimensional structure of dimeric human recombinant macrophage colony-stimulating factor. Science 258:1358-1362 (1992).

Parry et al., Conformational homologies among cytokines: interleukins and colony stimulating factors. J. Molecular Recognition 8: 107-110 (1988).

Powers et al., Three-dimensional solution structure of human interleukin-4 by multidimensional heteronuclear magnetic resonance spectroscopy. Science 256:1673-1677 (1992).

Rastetter, Enzyme engineering: applications and promise. Trends in Biotechnology, 1(3) 80-84 (1983).

Senda et al., Three-dimensional crystal structure of recombinant murine interferon-beta. EMBO J. 11: 3193-3201 (1992).

Smith et al., Human interleukin 4. The solution structure of a four-helix bundle protein. J. Mol. Biol. 224: 899-904 (1992).

Tsuchiya et al. Isolation and characterization of the cDNA for murine granulocyte colony-stimulating factor. Proc Natl Acad Sci USA. 83(20):7633-7637 (1986).

Weber et al., Physical principles of protein crystallization. In: Eisenberg (ed.), Advances in Protein Chemistry 41:1-33 (1991).

Wells et al., Additivity of mutational effects in proteins. Biochemistry 29(37): 8509-8517 (1990).

Welte et al., Purification and biochemical characterization of human pluripotent hematopoietic colony-stimulating factor. Proc. Natl. Acad. Sci. USA 82:1526-1530 (1985).

Sainathan SK, et al. PEGylated murine granulocyte-macrophage colony-stimulating factor: Production, purification, and characterization. Protein Expr Purif. Dec. 2005; 44(2):94-103.

International Search Report for PCT/DK2006/000292 mailed Dec. 1, 2006.

Brunger, Axel T. et al., "Crystallography & NMR system: a new software suite for macromolecular structure determination," Acta Cryst D54:905-921 (1998).

Cregut, David et al., "Molecular dynamics as a tool to detect protein foldability. A mutant of domain B1 of protein G with non-native secondary structure propensities," Protein Science 8:271-282 (1999).

Eisenberg, David et al., "The helical hydrophobic moment: a measure of the amphiphilicity of a helix," Nature 299: 371-378 (1982)9.

Emsley, Paul et al., "Coot: model-building tools for molecular graphics," Acta Cryst. D60:2126-2132 (2004).

Kabsch, Wolfgang et al., "Dictionary of protein secondary structure: pattern recognition of hydrogen-bonded and geometrical features," Biopolymers 22:2577-2637 (1983).

Kleywegt, Gerard J., "Use of non-crystallographic symmetry in protein structure refinement," Acta Cryst. D52:842-857 (1996).

Lau, Kit Fun et al., "Theory for protein mutability and biogenesis," PNAS 87:638-642 (1990).

Manavalan, Parthasarathy et al., "Sequence and structural relationships in the cytokine family," Journal of Protein Chemistry 11(3):321-331 (1992).

O'Shea, Erin K. et al., "X-ray structure of GCN4 leucine zipper, a two-stranded, parallel coiled coil," Science 254:539-544 (1991).

Ropson, Ira J. et al., "Properties and crystal structure of a beta-barrel folding mutant," Biophysical Journal 78:1551-1560 (2000).

Schiffer et al., "Use of helical wheels to represent the structures of proteins and to identify segments with helical potential," Biophysical Journal 7:121:135 (1967).

Shih, H. et al., "Structure of proteins with single-site mutations: a minimum perturbation approach," PNAS 82:1697-1700 (1985).

Tallquist, Michelle D. et al., "Degenerate recognition of alloantigenic peptides on a positive-selecting class I molecule," The Journal of Immunology 160:802-809 (1998).

Tsuji, Takashi et al., "Design and synthesis of the pseudo-EF hand in calbindin D9k: effect of amino acid substitutions in the a-helical regions," Proteins: Structure, Function and Genetics 9:12-22 (1991).

Zidovetzki, Raphael et al., "Transmembrane domains in the functions of Fc receptors," Biophysical Chemistry 100:555-575 (2003).

← 3 PEG

| Lane | |
|---|---|
| 1 | Molecular weight marker |
| 2 | After PEGylation |
| 3 | pH 9.5, T=0 h |
| 4 | pH 9.5, T=24 h |
| 5 | Upon application on cation exchange column |
| 6 | Flow-through from cation exchange |
| 7 | Purified product |

| Lane | |
|---|---|
| 1 | Molecular weight marker |
| 2 | After PEGylation |
| 3 | Diafiltered material, pH 9.5, T=0 h |
| 4 | pH 9.5, T=24 h |
| 5 | pH 9.5, T=42 h |

SEQUENCE LISTING

<160> NUMBER OF SEQ ID NOS: 1

<210> SEQ ID NO 1
<211> LENGTH: 174
<212> TYPE: PRT
<213> ORGANISM: Homo sapiens

<400> SEQUENCE: 1

```
Thr Pro Leu Gly Pro Ala Ser Ser Leu Pro Gln Ser Phe Leu Leu Lys
1               5                   10                  15

Cys Leu Glu Gln Val Arg Lys Ile Gln Gly Asp Gly Ala Ala Leu Gln
            20                  25                  30

Glu Lys Leu Cys Ala Thr Tyr Lys Leu Cys His Pro Glu Glu Leu Val
        35                  40                  45

Leu Leu Gly His Ser Leu Gly Ile Pro Trp Ala Pro Leu Ser Ser Cys
    50                  55                  60

Pro Ser Gln Ala Leu Gln Leu Ala Gly Cys Leu Ser Gln Leu His Ser
65                  70                  75                  80

Gly Leu Phe Leu Tyr Gln Gly Leu Leu Gln Ala Leu Glu Gly Ile Ser
                85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```

COMPOSITIONS COMPRISING POSITIONAL ISOMERS OF PEGYLATED G-CSF

CROSS-REFERENCE TO RELATED APPLICATIONS

This Application is a division of the U.S. patent application Ser. No. 11/420,546, now U.S. Pat. No. 7,381,805, which, pursuant to 35 U.S.C. §119(e), claims the benefit of U.S. Provisional Application Ser. No. 60/686,726 filed on Jun. 1, 2005, the disclosure of which is incorporated by reference herein in its entirety for all purposes.

FIELD OF THE INVENTION

The present invention relates to a method for removing labile PEG moieties from PEGylated G-CSF proteins to increase stability and uniformity, and to the resulting PEGylated G-CSF proteins. The invention also relates to pharmaceutical compositions comprising the PEGylated proteins and methods of treatment by administering the pharmaceutical compositions.

BACKGROUND OF THE INVENTION

The covalent attachment of polyethylene glycol (PEG) moieties to proteins or polypeptides ("PEGylation") is a well-known technique for improving the properties of such proteins or polypeptides, in particular pharmaceutical proteins, e.g. in order to improve circulation half-life and/or to shield potential epitopes and thus reduce the potential for an undesired immunogenic response. Numerous technologies based on activated PEG are available to provide attachment of the PEG moiety to one or more groups on the protein. For example, mPEG-succinimidyl propionate (mPEG-SPA, available from Nektar Therapeutics) is generally regarded as being selective for attachment to the N-terminus and epsilon-amino groups of lysine residues via an amide bond. However, in practice mPEG-SPA does not always attach exclusively to these groups, but may also attach to the hydroxyl group of a serine, tyrosine or threonine residue via an ester bond. As a result, PEGylated proteins prepared using this technology may not have a sufficient degree of uniformity and may contain a number of different PEG isomers other than those that were intended. This is undesired for various reasons, including the fact that it makes characterization of such proteins more complicated. Further, PEG moieties bound to groups other than those intended may be relatively unstable. For example, PEG moieties bound to a hydroxyl group via an ester bond in the case of an amine-specific PEG such as mPEG-SPA tend to be relatively unstable compared to those moieties that are bound via an amide bond to the N-terminal or a lysine residue. Depending on the formulation and storage conditions, this may lead to an undesired loss of these labile PEG groups and thus potentially to a change in the properties of the PEGylated protein over time. Further, there may be potential regulatory or safety issues for a PEGylated protein pharmaceutical in which there is a risk that one or more of the PEG moieties may detach from the protein in the body after it is administered to a patient.

The present invention addresses these problems by providing a method by which such labile PEG groups may be easily removed, thereby resulting in a more uniform and stable PEGylated protein product.

BRIEF DISCLOSURE OF THE INVENTION

The present invention relates generally to a method for increasing the stability and uniformity of a PEGylated polypeptide having at least one PEG moiety attached to a lysine residue or the N-terminal and at least one PEG moiety attached to a hydroxyl group, comprising subjecting the polypeptide to an altered pH for a period of time suitable to remove PEG moieties attached to a hydroxyl group, after which the pH is adjusted to a pH suitable for long-term storage of the polypeptide in question.

In a particular aspect, the invention relates to a method for increasing the stability and uniformity of a PEGylated granulocyte colony stimulating factor (G-CSF) polypeptide having at least one PEG moiety attached to the epsilon amino group of a lysine residue or the N-terminal amino group and at least one PEG moiety attached to a hydroxyl group, comprising subjecting the polypeptide to an elevated pH of above 8.0 for a period of time suitable to remove PEG moieties attached to a hydroxyl group, and reducing the pH to about 8.0 or lower.

Another aspect of the invention relates to a method for producing a PEGylated G-CSF polypeptide, comprising subjecting a G-CSF polypeptide to a PEGylation reaction with an amine-specific activated polyethylene glycol (PEG) to produce a PEGylated G-CSF polypeptide intermediate, and subsequently subjecting the PEGylated polypeptide intermediate to an elevated pH of at least about 9.0 for a period of time suitable to remove PEG moieties attached to a hydroxyl group to produce the PEGylated G-CSG polypeptide.

Another aspect of the invention relates to a composition comprising a homogeneous mixture of positional PEG isomers of a PEGylated G-CSF polypeptide variant, wherein at least about 80% of the positional PEG isomers of the mixture consist of two positional PEG isomers each having PEG moieties consisting of two PEG moieties bound to epsilon amino groups of lysine and one PEG moiety bound to the N-terminal amino group.

A further aspect of the invention relates to a composition comprising a mixture of positional PEG isomers of a PEGylated G-CSF polypeptide, wherein the polypeptide comprises the substitutions K16R, K34R, K40R, T105K and S159K relative to wild-type human G-CSF (SEQ ID NO:1), and wherein at least about 80% of the positional PEG isomers of the polypeptide are lysine/N-terminal positional PEG isomers having three attached PEG moieties.

In a still further aspect the invention relates to a method of producing a mixture of lysine/N-terminal positional PEG isomers of a recombinant G-CSF polypeptide comprising the substitutions K16R, K34R, K40R, T105K and S159K relative to wild-type human G-CSF, comprising: a) expressing the recombinant G-CSF polypeptide in a host cell; b) isolating the recombinant G-CSF polypeptide; c) reacting the isolated recombinant G-CSF polypeptide with an amine-specific activated PEG to produce a plurality of positional PEG isomers of the recombinant G-CSF polypeptide; d) reacting the plurality of positional PEG isomers at a pH of 8.5 to 10.5 to produce a plurality of partially dePEGylated lysine/N-terminal positional PEG isomers of the recombinant G-CSF polypeptide.

Further aspects of the invention relate to PEGylated G-CSF polypeptides produced using the methods described herein, as well as PEGylated G-CSF polypeptides characterized by their positional PEG isomer distribution and compositions comprising such PEGylated G-CSF polypeptides, and methods for increasing the level of neutrophils in a patient suffering from or at risk of an insufficient neutrophil level by administering a PEGylated G-CSF polypeptide or a composition of the invention. Additional aspects of the invention and preferred embodiments will be apparent from the description below as well as from the appended claims.

DESCRIPTION

Definitions

Figure 1:
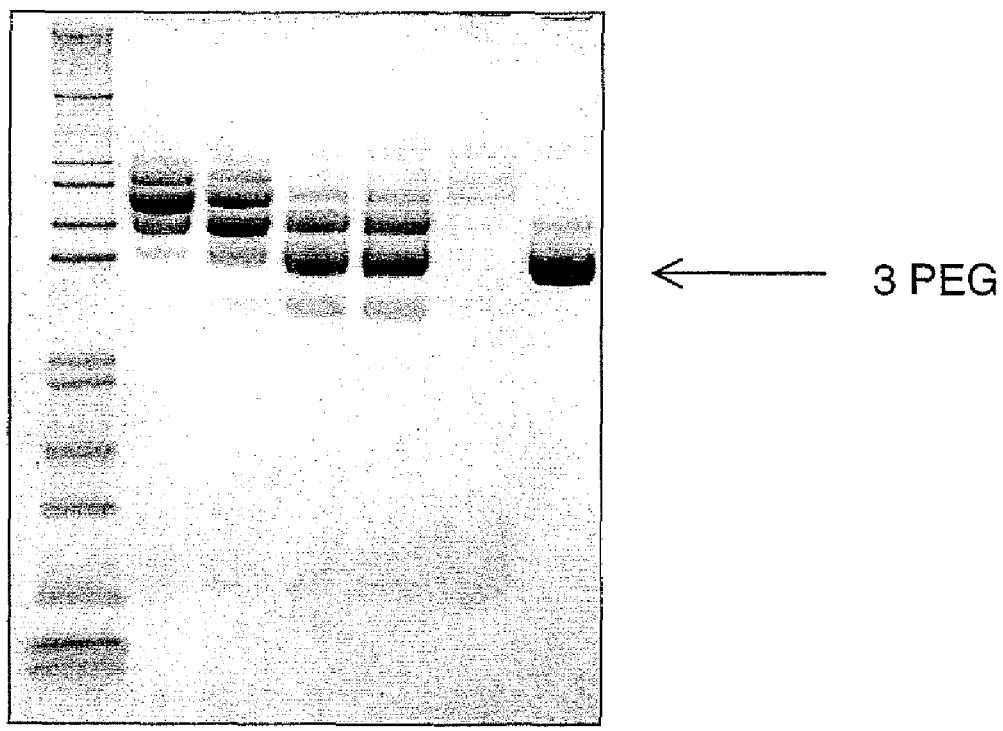
FIG. 1 shows a scan of an SDS-PAGE analysis of a G-CSF variant that was PEGylated, partially de-PEGylated, and purified as described herein.

In the context of the present description and claims the following definitions apply:

The terms "polypeptide" or "protein" may be used interchangeably herein to refer to polymers of amino acids, without being limited to an amino acid sequence of any particular length. These terms are intended to include not only full-length proteins but also e.g. fragments or truncated versions, variants, domains, etc. of any given protein or polypeptide.

A "G-CSF" polypeptide is a polypeptide having the sequence of human granulocyte colony stimulating factor (hG-CSF) as shown in SEQ ID NO:1, or a variant of hG-CSF that exhibits G-CSF activity. The "G-CSF activity" may be the ability to bind to a G-CSF receptor (Fukunaga et al., *J. Bio. Chem.*, 265:14008, 1990), but is preferably G-CSF cell proliferation activity, in particular determined in an in vitro activity assay using the murine cell line NFS-60 (ATCC Number: CRL-1838). A suitable in vitro assay for G-CSF activity using the NFS-60 cell line is described in by Hammerling et al. in *J. Pharm. Biomed. Anal.* 13(1):9-20, 1995. A polypeptide "exhibiting" G-CSF activity is considered to have such activity when it displays a measurable function, e.g. a measurable proliferative activity in the in vitro assay.

A "variant" is a polypeptide which differs in one or more amino acid residues from a parent polypeptide, where the parent polypeptide is generally one with a native, wild-type amino acid sequence, typically a native mammalian polypeptide, and more typically a native human polypeptide. The variant thus contains one or more substitutions, insertions or deletions compared to the native polypeptide. These may, for example, include truncation of the N- and/or C-terminus by one or more amino acid residues, or addition of one or more extra residues at the N- and/or C-terminus, e.g. addition of a methionine residue at the N-terminus. The variant will most often differ in up to 15 amino acid residues from the parent polypeptide, such as in up to 12, 10, 8 or 6 amino acid residues.

An "amine-specific activated PEG" is any activated PEG derivative that preferentially attaches to the N-terminal amino group or the ε-amino groups of lysine residues via an amide bond. Examples of amine-specific activated PEG derivatives include:

mPEG-succinimidyl propionate (mPEG-SPA):

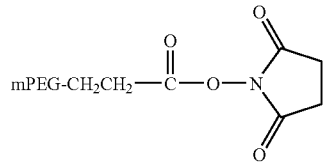

mPEG-succinimidyl butanoate (mPEG-SBA):

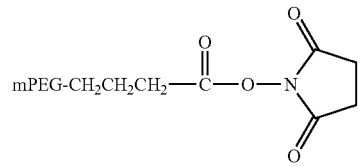

and mPEG-succinimidyl α-methylbutanoate (mPEG-SMB):

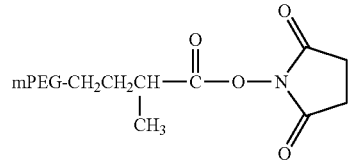

mPEG-SPA, mPEG-SBA and mPEG-SMB are available from Nektar Therapeutics; see the Nektar Advanced PEGylation Catalogs 2004 and 2005-2006, "Polyethylene Glycol and Derivatives for Advanced PEGylation". Other amine-specific activated PEG derivatives include PEG-SS (Succinimidyl Succinate), PEG-SG (Succinimidyl Glutarate), PEG-NPC (p-nitrophenyl carbonate), and PEG-isocyanate, available from SunBio Corporation; and PEG-SCM, available from NOF Corporation.

A "labile" PEG moiety refers in the present context to a PEG moiety attached to a hydroxyl group of a polypeptide, in particular via an ester bond to the hydroxyl group of a serine, tyrosine or threonine residue. As explained above, the attachment of such PEG moieties via a hydroxyl group tends to be unstable, so that these PEG moieties tend to detach from the polypeptide over time through hydrolysis of the ester bonds, e.g. when a polypeptide containing such moieties is stored in the form of an aqueous solution.

As used herein, "stability" refers to the stability of the attachment of PEG moieties bound to a polypeptide, i.e. whether such PEG moieties remain bound to the polypeptide over time, e.g. during storage in an aqueous solution, or whether they tend to detach e.g. as a result of ester bond hydrolysis.

As used herein the term "positional PEG isomer" of a protein refers to different PEGylated forms of the protein where PEG groups are located at different amino acid positions of the protein. The term "lysine/N-terminal PEG isomer" of a protein means that the PEG groups are attached to the amino-terminal of the protein and/or to epsilon amino groups of lysine residues in the protein. For example, the phrase "lysine/N-terminal positional PEG isomers having 3 attached PEG moieties", as applied to G-CSF, means a mixture of G-CSF positional PEG isomers in which three PEG groups are attached to epsilon amino groups of lysine residues and/or to the N-terminus of the protein. Typically, a "lysine/N-terminal positional PEG isomer having 3 attached PEG moieties" will have two PEG moieties attached to lysine residues and one PEG moiety attached to the N-terminus. Analysis of the positional PEG isomers may be performed using cation exchange HPLC as described in the examples below.

A "substantially purified mixture of lysine/N-terminal positional PEG isomers" of a polypeptide refers to mixture of lysine/N-terminal positional PEG isomers which has been subjected to a chromatographic or other purification procedure in order to remove impurities such as non-lysine/N-terminal positional PEG isomers. The "substantially purified mixture of lysine/N-terminal positional PEG isomers" will, for example, be free of most labile PEG moieties attached to a hydroxyl group that would otherwise be present in the absence of a partial de-PEGylation step and subsequent purification as described herein, and will typically contain less than about 20% polypeptides containing a labile PEG moiety attached to a hydroxyl group, more typically less than about 15%. Preferably, there will be less than about 10% polypeptides containing a labile PEG moiety attached to a hydroxyl group, for example less than about 5%.

The term "homogeneous mixture of positional PEG isomers of a polypeptide variant" means that the polypeptide moiety of the different positional PEG isomers is the same. This means that the different positional PEG isomers of the mixture are all based on a single polypeptide variant sequence. For example, a homogeneous mixture of positional PEG isomers of a PEGylated G-CSF polypeptide variant means that different positional PEG isomers of the mixture are based on a single G-CSF polypeptide variant.

As used herein, "uniformity" refers to the homogeneity of a PEGylated polypeptide in terms of the number of different positional isomers, i.e. different polypeptide isomers containing different numbers of PEG moieties attached at different positions, as well as the relative distribution of these positional isomers. For pharmaceutical polypeptides intended for therapeutic use in humans or animals, it is generally desirable that the number of different positional PEG isomers is minimized.

"Partial de-PEGylation" refers to the fact that the methods of the invention serve to remove labile PEG moieties attached to a hydroxyl group, while PEG moieties that are more stably attached to the N-terminal or the amino group of a lysine residue remain intact. As explained below, the progress of the de-PEGylation process is dependent upon the particular elevated pH value and the duration at the elevated pH. Therefore, depending on the conditions chosen in any particular case, it is possible that a small proportion of the polypeptides can still have a PEG moiety attached to a hydroxyl group at the end of a de-PEGylation step. Based on the information provided herein and common general knowledge in the art of protein analysis, however, persons skilled in the art will be able to adapt the process so that substantially all labile PEG moieties are removed and any remaining labile PEG moieties are insignificant for the desired properties of the final product. Any reference to "de-PEGylation" herein should be understood to refer to "partial de-PEGylation".

DETAILED DESCRIPTION

As indicated above, one particular aspect of the invention relates to a method for increasing the stability and uniformity of a PEGylated G-CSF polypeptide having at least one PEG moiety attached to the epsilon amino group of a lysine residue or the N-terminal amino group and at least one PEG moiety attached to a hydroxyl group, comprising subjecting the polypeptide to an elevated pH of above 8.0 for a period of time suitable to remove PEG moieties attached to a hydroxyl group, and reducing the pH to about 8.0 or lower. Although this method is suitable for any mammalian G-CSF polypeptide, the polypeptide is preferably a human G-CSF polypeptide, i.e. with the amino acid sequence of SEQ ID NO:1, optionally with a methionine residue added at the N-terminal, or a variant thereof. In the case of G-CSF variants, these may have one or more substitutions, insertions or deletions, and/or truncation of the N- and/or C-terminus by one or more amino acid residues, compared to a native, wild-type G-CSF polypeptide, typically compared to human G-CSF (SEQ ID NO:1), for example from 1 to 15 substitutions, such as up to 6, 8, 10 or 12 substitutions. Preferred G-CSF variants include those disclosed in WO 01/51510 and WO 03/006501.

As it is described e.g. in WO 03/006501, hG-CSF contains four lysine residues in positions 16, 23, 34 and 40, and when subjecting G-CSF to PEGylation using activated PEG that preferentially binds to lysine residues or the N-terminal it will often be desirable to remove at least one of these lysine residues, e.g. two, three or all of these residues, e.g. by deletion but preferably by substitution. The G-CSF polypeptide used in the method of the invention may therefore be a variant in which at least one of the amino acid residues selected from the group consisting of K16, K23, K34 and K40 has been deleted or substituted with another amino acid residue. Typically, removal of a lysine residue will be by substitution, generally by substitution with an R or Q residue, preferably an R residue. The G-CSF polypeptide may thus have one, two, three or four substitutions selected from the group consisting of K16R/Q, K23R/Q, K34R/Q, K40R/Q (where, for example, "K16R/Q" denotes that the lysine in position 16 is substituted with either an arginine or a glutamine residue). Preferably, the polypeptide includes the substitutions K16R+K34R+K40R, while the lysine in position 23 is left unaltered.

Along with removal of lysine residues where PEGylation is not desired, WO 03/006501 also describes addition of lysine residues in order to create sites for PEGylation. These may be added by insertion but are preferably added by substitution. Examples of preferred amino acid substitutions in order to introduce a site for PEGylation include one or more of Q70K, Q90K, T105K, Q120K, T133K, S159K and H170K, such as two, three, four or five of these substitutions, with preferred substitutions being T105K+S159K. In a preferred embodiment the G-CSF polypeptide includes the substitutions K16R, K34R, K40R, T105K and S159K. In a particular embodiment, the G-CSF polypeptide has only these five substitutions relative to hG-CSF.

Production of G-CSF Polypeptides

The G-CSF polypeptides to be PEGylated in accordance with the invention may be produced by any suitable method known in the art, for example as described in WO 03/006501, which is hereby incorporated by reference. Such methods include constructing a nucleotide sequence encoding the polypeptide and expressing the sequence in a suitable transformed or transfected host. However, polypeptides of the invention may be produced, albeit less efficiently, by chemical synthesis or a combination of chemical synthesis or a combination of chemical synthesis and recombinant DNA technology. A nucleotide sequence encoding a polypeptide or the polypeptide part of a conjugate of the invention may be constructed by isolating or synthesizing a nucleotide sequence encoding the parent G-CSF, such as hG-CSF with the amino acid sequence shown in SEQ ID NO:1, and then changing the nucleotide sequence so as to effect introduction (i.e. insertion or substitution) or deletion (i.e. removal or substitution) of the relevant amino acid residue(s).

The nucleotide sequence is conveniently modified by site-directed mutagenesis in accordance with conventional methods. Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction (LCR) (Barany, PNAS 88:189-193, 1991). The individual oligonucleotides typically contain 5' or 3' overhangs for complementary assembly.

Once assembled (by synthesis, site-directed mutagenesis or another method), the nucleotide sequence encoding the polypeptide is inserted into a recombinant vector and operably linked to control sequences necessary for expression of the G-CSF in the desired transformed host cell.

Persons skilled in the art will be capable of selecting suitable vectors, expression control sequences and hosts for expressing the polypeptide. The recombinant vector may be an autonomously replicating vector, i.e. a vector, which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature. Detailed information on suitable vectors for expressing G-CSF may be found in WO 03/006501.

The term "control sequences" is defined herein to include all components which are necessary or advantageous for the expression of the polypeptide of the invention. Each control sequence may be native or foreign to the nucleic acid sequence encoding the polypeptide. Such control sequences include, but are not limited to, a leader sequence, polyadenylation sequence, propeptide sequence, promoter, enhancer or upstream activating sequence, signal peptide sequence, synthetic intron, and transcription terminator. At a minimum, the control sequences include a promoter. A wide variety of expression control sequences may be used in the present invention, e.g. any of the control sequences disclosed in WO 03/006501.

The nucleotide sequence of the invention encoding a polypeptide exhibiting G-CSF activity, whether prepared by site-directed mutagenesis, synthesis, PCR or other methods, may optionally also include a nucleotide sequence that encodes a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with hG-CSF) or heterologous (i.e. originating from another source than hG-CSF) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as E. coli, or eukaryotic, e.g. derived from a mammalian, or insect or yeast cell. For further information on suitable signal peptides, see WO 03/006501.

Any suitable host may be used to produce the G-CSF polypeptide, including bacteria (although not particularly preferred), fungi (including yeasts), plant, insect, mammal, or other appropriate animal cells or cell lines, as well as transgenic animals or plants. Mammalian cells are preferred. Examples of bacterial host cells include gram-positive bacteria such as strains of Bacillus, e.g. B. brevis or B. subtilis, Pseudomonas or Streptomyces, or gram-negative bacteria, such as strains of E. coli. Examples of suitable filamentous fungal host cells include strains of Aspergillus, e.g. A. oryzae, A. niger, or A. nidulans, Fusarium or Trichoderma. Examples of suitable yeast host cells include strains of Saccharomyces, e.g. S. cerevisiae, Schizosaccharomyces, Klyveromyces, Pichia, such as P. pastoris or P. methanolica, Hansenula, such as H. Polymorpha or Yarrowia. Examples of suitable insect host cells include a Lepidoptora cell line, such as Spodoptera frugiperda (Sf9 or Sf21) or Trichoplusioa ni cells (High Five) (U.S. Pat. No. 5,077,214). Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)). Additional suitable cell lines are known in the art and available from public depositories such as the American Type Culture Collection, Rockville, Md.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered by methods known in the art. For example, the polypeptide may be recovered from the nutrient medium by conventional procedures including, but not limited to, centrifugation, filtration, extraction, spray drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989). Specific methods for purifying polypeptides exhibiting G-CSF activity are described by D. Metcalf and N. A. Nicola in *The hemopoietic colony-stimulating factors*, p.

50-51, Cambridge University Press (1995), by C. S. Bae et al., Appl. Microbiol. Biotechnol, 52:338-344 (1999) and in U.S. Pat. No. 4,810,643.

PEGylation

The purified G-CSF polypeptides can then be PEGylated by a variety of methods known to one of ordinary skill in the art. For example, a G-CSF polypeptide can be subjected to PEGylation with an amine-specific activated polyethylene glycol (PEG).

The amine-specific activated PEG may be any of those mentioned above, for example mPEG-succinimidyl propionate (mPEG-SPA), mPEG-succinimidyl butanoate (mPEG-SBA), or mPEG-succinimidyl α-methylbutanoate (mPEG-SMB). The molecular weight of the PEG moieties may be selected based e.g. on the number of PEG moieties to be attached to the polypeptide and will often be in the range of from about 1 kDa to about 20 kDa, such as from about 1 kDa to about 12 kDa, e.g. from about 2 kDa to about 10 kDa, such as from about 4 kDa to about 6 kDa, e.g. about 5 kDa. For example, the activated PEG may be mPEG-SPA with a molecular weight of about 5 kDa. PEGylation may, for example, be performed at a pH of about 7.5-9.0, e.g. about 8.0-8.5. When used about PEG moieties herein, the word "about" indicates an approximate average molecular weight and reflects the fact that there will normally be a certain molecular weight distribution in a given polymer preparation. For further general information on PEGylation methods see, for example, the Nektar Advanced PEGylation Catalogs 2004 and 2005-2006, as well as the references cited therein. A more detailed description of PEGylation methods for G-CSF polypeptides is also provided in WO 03/006501.

Partial De-PEGylation

The choice of an elevated pH for the de-PEGylation step is made based on factors such as the temperature at which the de-PEGylation step takes place, the duration of the de-PEGylation step, and the conditions that were used for PEGylation, including the pH at which PEGylation was performed. Generally, the higher the pH used during de-PEGylation, the faster the de-PEGylation takes place. Persons skilled in the art will thus realize that de-PEGylation conditions such as pH, time and temperature can be adjusted to each other to obtain the desired result in any given situation. For example, although it is possible to use a relatively low elevated pH of e.g. between 8 and 9, use of a higher pH of e.g. between 9 and 11, such as between 9 and 10, will result in a faster de-PEGylation. Typically, the elevated pH will therefore be in the range of from about 8.5 to about 11.0, e.g. from about 8.5 to about 10.5, such as from about 9.0 to about 10.0. The elevated pH may, for example, be in the range of from about 9.2 to about 9.8, e.g. about 9.5.

Normally, the de-PEGylation step will take place immediately following PEGylation, as this will generally be most efficient and result in shorter processing times and higher yields. In its basic version, the invention is thus characterized by partial de-PEGylation of a PEGylated bulk intermediate, followed by conventional separation using e.g. chromatographic purification as described below. If desired for any reason, however, the PEGylation procedure may be followed by an intermediate purification step prior to de-PEGylation. The intermediate purification step may, e.g., comprise chromatographic purification as described below followed by ultrafiltration and/or diafiltration. The intermediate product obtained from any such intermediate purification procedure may, if desired, be stored prior to de-PEGylation and any subsequent purification steps. In this case, the intermediate PEGylated product may e.g. be stored by freezing or lyophilization using methods generally known in the art.

The de-PEGylation may be performed at any temperature which is otherwise suitable for the polypeptide in question, for example from about 5° C. to about 40° C., such as from about 10° C. to about 35° C. The de-PEGylation will often be performed at a temperature of from about 15° C. to about 25° C., e.g. at an ambient temperature of about 20-22° C.

As explained above, the duration of the de-PEGylation step at an elevated pH to obtain a desired result will depend on other factors such as pH and temperature, but will generally be in the range of from about 2 hours to about 100 hours, typically from about 4 hours to about 72 hours, more typically from about 8 hours to about 48 hours. Since it will normally be desirable to perform the de-PEGylation step in as short a time as possible, the polypeptide will often be subjected to the elevated pH for a period of not more than about 24 hours, e.g. from about 12 hours to about 30 hours, such as from about 18 to about 24 hours. As indicated above, a relatively short de-PEGylation period at the elevated pH will generally be accompanied by a relatively high pH, e.g. about 9-10.

Following the de-PEGylation at an elevated pH, the pH is reduced to about 8.0 or lower, the particular pH being chosen according to the intended storage conditions for the polypeptide. For G-CSF, a suitable pH for long-term storage will often be in the range of from about 2.0 to about 5.0, for example from about 2.5 to about 4.5, such as about 4.0. In some cases, depending e.g. on the particular formulation to be used, a somewhat higher pH may be chosen, i.e. a pH of about 5.0-8.0, e.g. about 6.0-7.5, such as about 7.0-7.5. Various pharmaceutical formulations of G-CSF are described, e.g., in U.S. Pat. Nos. 5,104,651, 5,919,757, 6,497,869 and 6,776,983.

For adjustment of pH in the context of the present invention, any suitable acid or base may be used, both organic or inorganic acids and bases. Similarly, any suitable buffer may be used for maintaining the pH at a desired level. Persons skilled in the art will be familiar with acids, bases and buffers suitable for use in any given situation, depending e.g. on the polypeptide in question and the desired pH.

Subsequent to reduction of the pH, the polypeptide will generally be subjected to at least one chromatographic purification step, for example ion exchange chromatography or gel filtration chromatography, in order to separate polypeptides having a desired number of PEG groups attached. The chromatographic purification may be carried out using methods generally known in the art. For example, where the reduced pH following de-PEGylation is below about 7.0, cation exchange chromatography may be used. Alternatively or additionally, chromatography may be performed prior to reduction of the pH, using anion exchange chromatography at the elevated pH value. Further purification as well as any desired analysis of the product may similarly be performed using standard methods known in the art. For example, further purification subsequent to the chromatographic purification step may be performed using e.g. ultrafiltration or diafiltration.

As mentioned above, another aspect of the invention relates to a method for producing a PEGylated G-CSF polypeptide, comprising subjecting a G-CSF polypeptide to PEGylation with an amine-specific activated polyethylene glycol (PEG), and subsequently subjecting the PEGylated polypeptide to an elevated pH of at least about 9.0 for a period of time suitable to remove PEG moieties attached to a hydroxyl group. This method results in a PEGylated G-CSF polypeptide having at least one PEG moiety attached to the epsilon amino group of a lysine residue or the N-terminal amino group and substantially no PEG moieties attached to a hydroxyl group. In one embodiment, this aspect of the invention is performed using PEGylation at a pH of about 7.0-9.0, after which the pH is increased to remove labile PEG moieties. In another embodiment, PEGylation may be performed at a higher pH of above 9.0, such as a pH in the range of 9-11, such as from about 9.2 to 10.0, e.g. about 9.5. In this case, PEGylation and de-PEGylation may be performed as a single step at a single pH value for a sufficient period of time to result in the desired PEGylation at the N-terminus and lysine residues while avoiding undesired binding of PEG moieties to hydroxyl groups.

The amine-specific activated PEG may be any of those mentioned above, for example mPEG-succinimidyl propionate (mPEG-SPA), mPEG-succinimidyl butanoate (mPEG-SBA), or mPEG-succinimidyl α-methylbutanoate (mPEG-SMB). The molecular weight of the PEG moieties will similarly be as described above, e.g. in the range of from about 1 kDa to about 20 kDa, such as from about 1 kDa to about 12 kDa, e.g. from about 2 kDa to about 10 kDa, such as from about 4 kDa to about 6 kDa, e.g. about 5 kDa. For example, the activated PEG may be mPEG-SPA with a molecular weight of about 5 kDa. PEGylation may, for example, be performed at a pH of about 7.5-9.0, e.g. about 8.0-8.5. Depending on the pH used during PEGylation, the elevated pH chosen will also be similar to the ranges generally described above, for example in the range of from about 9.2 to 11.0, such as from about 9.2 to 10.0. Similarly, the time period at the elevated pH may also be chosen as described above, and the same applies to subsequent purification, etc.

The method described herein provides a number of advantages for production processes aimed at producing a uniform and stable PEGylated protein, including the fact that it is simple and fast, requiring only a single extra step of altered pH for a limited time period, and there is no need to otherwise change the PEGylation or purification procedures used in a given production process. For this reason, the same general procedure of an altered pH for a period of time sufficient to remove labile PEG groups may be used for the production of any PEGylated protein. In general, either a basic or acidic pH may be used for removing labile PEG moieties attached to a hydroxyl group, with the detachment of the labile PEG moieties taking place faster when the pH is more acidic (for an acid pH) or more basic (for a basic pH). The choice of conditions for obtaining labile PEG detachment will be made based on e.g. the structural features of the particular protein, including the microenvironment of attachment sites for PEG moieties.

PEGylated G-CSF Polypeptides

As indicated above, the method of the present invention is advantageous in that it results in an increased homogeneity of the PEGylated polypeptide in terms of the number of different positional PEG isomers. Depending on the number of attachment groups and the particular PEGylation chemistry being used, the method allows the isolation of PEGylated G-CSF that is more uniform and more stable during storage than would otherwise be possible. For example, it has been found that for a PEGylated G-CSF polypeptide having the substitutions K16R, K34R, K40R, T105K and S159K relative to wild-type human G-CSF, it is possible to obtain a product wherein at least about 90-95% of the positional PEG isomers of the polypeptide have 3 attached PEG moieties.

Another embodiment of the invention relates to a composition comprising a homogeneous mixture of positional PEG isomers of a PEGylated G-CSF polypeptide variant, wherein at least about 80%, preferably at least about 85%, more preferably at least about 90%, for example at least about 95% of the positional PEG isomers of the mixture consist of two positional PEG isomers each having PEG moieties consisting of two PEG moieties bound to epsilon amino groups of lysine residues and one PEG moiety bound to the N-terminal amino group.

Another embodiment of the invention thus relates to a PEGylated G-CSF polypeptide comprising the substitutions K16R, K34R, K40R, T105K and S159K relative to wild-type human G-CSF, wherein at least about 80% of the positional PEG isomers of the polypeptide have 3 attached PEG moieties. Typically, the proportion of the positional PEG isomers having 3 attached PEG moieties will be greater than 80%, such as at least about 85% or at least about 90%, and may be even higher, such as at least about 91%, at least about 92%, at least about 93%, at least about 94%, or at least about 95%. In yet another embodiment, the invention relates to a PEGylated G-CSF polypeptide containing only the substitutions K16R, K34R, K40R, T105K and S159K relative to wild-type human G-CSF, and wherein at least about 80% of the positional PEG isomers of the polypeptide have 3 attached PEG moieties. Typically, the proportion of the positional PEG isomers having 3 attached PEG moieties will be greater than 80%, such as at least about 85% or at least about 90%, and may be even higher, such as at least about 91%, at least about 92%, at least about 93%, at least about 94%, or at least about 95%.

In a still further embodiment, the invention relates to a composition comprising a mixture of PEGylated G-CSF polypeptides comprising the substitutions K16R, K34R, K40R, T105K and S159K relative to wild type human G-CSF, wherein at least about 80%, preferably at least about 85%, more preferably at least about 90%, such as at least about 95% of the PEGylated G-CSF polypeptides in the mixture are composed of two positional PEG G-CSF isomers each containing three PEG groups, wherein one of the isomers has PEG groups attached at the N-terminal, Lys23 and Lys159 and the other isomer has PEG groups attached at the N-terminal, Lys105 and Lys159. In yet another embodiment, the invention relates to a composition comprising a mixture of PEGylated G-CSF polypeptides containing only the substitutions K16R, K34R, K40R, T105K and S159K relative to wild type human G-CSF, and wherein at least about 80%, preferably at least about 85%, more preferably at least about 90%, such as at least about 95% of the PEGylated G-CSF polypeptides in the mixture are composed of two positional PEG G-CSF isomers each containing three PEG groups, wherein one of the isomers has PEG groups attached at the N-terminal, Lys23 and Lys159 and the other isomer has PEG groups attached at the N-terminal, Lys105 and Lys159

It has been found that PEGylated G-CSF polypeptides produced according to the invention are highly storage-stable with respect to their degree of PEGylation. As it is shown in the examples below, aqueous formulations of such PEGylated G-CSF polypeptides are able to be stored for an extended period of time with a largely unaltered PEGylation pattern. This was in particular the case when the compositions were stored at a temperature of 5° C., but surprisingly the compositions were found to be relatively stable even when stored at a high temperature of 25° C. or 35° C.

A further aspect of the invention therefore relates to a storage-stable PEGylated G-CSF polypeptide comprising the substitutions K16R, K34R, K40R, T105K and S159K relative to wild-type human G-CSF, wherein at least about 80% of the positional PEG isomers of the polypeptide have 3 attached PEG moieties after storage in an aqueous reference composition for 3 months at a temperature of 5° C. Typically, the proportion of the positional PEG isomers having 3 attached PEG moieties after storage for 3 months at a temperature of 5° C. will be greater than 80%, such as at least about 85% or at least about 90%. In some cases, this proportion may even higher, such as at least about 91%, at least about 92%, at least about 93%, at least about 94%, or at least about 95%. For purposes of determining the stability of a PEGylated G-CSF polypeptide produced according to the invention, the stability may be tested as described in Example 4, for example using one of formulations A, B, C or D described therein as the reference composition, in particular formulation D.

Pharmaceutical Compositions

Another aspect of the invention relates to pharmaceutical compositions comprising a PEGylated G-CSF polypeptide according to the invention. One embodiment of the invention thus relates to a composition comprising a pharmaceutically acceptable carrier and a PEGylated G-CSF polypeptide, wherein the polypeptide comprises the substitutions K16R, K34R, K40R, T105K and S159K relative to wild-type human G-CSF (SEQ ID NO:1), and wherein at least about 80% of the positional PEG isomers of the polypeptide have 3 attached PEG moieties. Typically, the proportion of the positional PEG isomers having 3 attached PEG moieties will be at least about 85%, preferably at least about 90%, and may be even higher, such as at least about 91%, at least about 92%, at least about 93%, at least about 94%, or at least about 95%. In yet another embodiment, the invention relates to a pharmaceutical composition comprising a pharmaceutically acceptable carrier and a PEGylated G-CSF polypeptide, wherein the polypeptide contains only the substitutions K16R, K34R, K40R, T105K and S159K relative to wild-type human G-CSF (SEQ ID NO:1), and wherein at least about 80% of the positional PEG isomers of the polypeptide have 3 attached PEG moieties. Typically, the proportion of the positional PEG isomers having 3 attached PEG moieties will be at least about 85%, preferably at least about 90%, and may be even higher, such as at least about 91%, at least about 92%, at least about 93%, at least about 94%, or at least about 95%.

Another embodiment of the invention relates to a pharmaceutical composition comprising a homogeneous mixture of positional PEG isomers of a PEGylated G-CSF polypeptide variant, wherein at least about 80%, preferably at least about 85%, more preferably at least about 90%, for example at least about 95% of the positional PEG isomers of the mixture consist of two positional PEG isomers each having PEG moieties consisting of two PEG moieties bound to epsilon amino groups of lysine residues and one PEG moiety bound to the N-terminal amino group.

In a further embodiment the invention relates to pharmaceutical compositions comprising a pharmaceutically acceptable carrier and a mixture of PEGylated G-CSF polypeptides comprising the substitutions K16R, K34R, K40R, T105K and S159K relative to wild type human G-CSF, wherein at least about 80%, preferably at least about 85%, more preferably about 90%, such as at least about 95% of the PEGylated G-CSF polypeptides in the mixture are composed of two positional PEG G-CSF isomers each containing three PEG groups, wherein one of the isomers has PEG groups attached at the N-terminal, Lys23 and Lys159 and the other isomer has PEG groups attached at the N-terminal, Lys105 and Lys159. In yet another embodiment, the invention, the invention relates to pharmaceutical compositions comprising a pharmaceutically acceptable carrier and a mixture of PEGylated G-CSF polypeptides containing only the substitutions K16R, K34R, K40R, T105K and S159K relative to wild type human G-CSF, wherein at least about 80%, preferably at least about 85%, more preferably about 90%, such as at least about 95% of the PEGylated G-CSF polypeptides in the mixture are composed of two positional PEG G-CSF isomers each containing three PEG groups, wherein one of the isomers has PEG groups attached at the N-terminal, Lys23 and Lys159 and the other isomer has PEG groups attached at the N-terminal, Lys105 and Lys159

Pharmaceutical compositions comprising the G-CSF polypeptide of the invention may be formulated in a variety of forms, e.g. in lyophilised form or, preferably, in a stable liquid formulation, typically as an aqueous formulation. Such compositions typically comprise one or more components selected from buffering agents, preservatives, isotonicifiers, stabilizers, non-ionic surfactants or detergents, and additional miscellaneous excipients such as bulking agents or fillers, chelating agents, antioxidants and cosolvents. One example of a suitable formulation for G-CSF is that used for Neulasta® (pegfilgrastim), which is supplied in an aqueous solution with a pH of 4.0 containing, per 0.6 ml, 0.35 mg acetate, 30.0 mg sorbitol, 0.02 mg polysorbate 20, and 0.02 mg sodium.

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution. The compositions of the invention are preferably in the form of an aqueous solution, however.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which may be termed "excipients"), for example buffering agents, stabilizing agents, preservatives, isotonifiers, non-ionic detergents, antioxidants and/or other miscellaneous additives.

Buffering agents help to maintain the pH in a desired range. They are typically present at a concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gly-uconate mixture, etc.), oxalate buffers (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and when present are typically added in amounts of about 0.2%-1% (w/v). Suitable preservatives include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers may e.g. be present in the range of from 0.1 to 10,000 parts by weight based on the active protein weight.

Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Additional miscellaneous excipients that may be added include bulking agents or fillers (e.g. starch), chelating agents (e.g. EDTA), antioxidants (e.g., ascorbic acid, methionine, vitamin E) and cosolvents.

The active ingredient may also be entrapped in microcapsules prepared, for example, by coacervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions.

Parenteral formulations to be used for in vivo administration must be sterile. This is readily accomplished by methods well-known in the art, for example, by filtration through sterile filtration membranes.

Therapeutic Methods

Another aspect of the invention relates to therapeutic methods and methods for the manufacture of a medicament using the PEGylated G-CSF polypeptide of the invention. Leukopenia (a reduced level of white blood cells) and neutropenia (a reduced level of neutrophils) are disorders that result in an increased susceptibility to various types of infections. Neutropenia can be chronic, e.g. in patients infected with HIV, or acute, e.g. in cancer patients undergoing chemotherapy or radiation therapy. For patients with severe neutropenia, e.g. as a result of chemotherapy, even relatively minor infections can be serious, and neutropenia will often require an interruption in the chemotherapy protocol. The PEGylated G-CSF polypeptides of the invention are particularly suitable for prevention or treatment of infection in cancer patients undergoing certain types of chemotherapy, radiation therapy and bone marrow transplantations, mobilisation of progenitor cells for collection in peripheral blood progenitor cell transplantations, treatment of severe chronic or relative leukopenia, treatment of patients with acute myeloid leukemia, treatment of AIDS or other immunodeficiency diseases, and for antifungal therapy, in particular for treatment of systemic or invasive candidiasis. A "patient" for the purposes of the present invention includes both humans and other mammals, although the therapeutic methods of the invention are primarily aimed at treatment of human patients.

This aspect of the invention thus relates to a method for increasing the level of neutrophils in a patient suffering from or at risk of an insufficient neutrophil level, comprising administering to said patient an effective dose of a PEGylated G-CSF polypeptide as described above, or a pharmaceutical composition as described above comprising the PEGylated G-CSF polypeptide. In one embodiment of this aspect of the invention, the patient suffering from or at risk of an insufficient neutrophil level is a cancer patient, in particular a cancer patient being treated with chemotherapy or radiation therapy, especially chemotherapy.

The PEGylated G-CSF polypeptides of the invention are contemplated to be useful for stimulating production of neutrophils in patients suffering from a variety of different types of cancer, including breast cancer, non-small cell lung cancer, small cell lung cancer, colorectal cancer, uterine cancer, ovarian cancer, non-Hodgkin's lymphoma (NHL) and Hodgkin's disease. Similarly, the polypeptides of the invention are contemplated for administration to patients receiving any of a variety of different types of chemotherapeutic agents, including:

alkylating agents, e.g. mustard gas derivatives, such as Cyclophosphamide, Chlorambucil, Ifosfamide, Mechlorethamine or Melphalan; ethylenimines, such as Hexamethylmelamine or Thiotepa; alkylsulfonates such as Busulfan; hydrazines and triazines such as Altretamine, Dacarbazine, Procarbazine or Temozolomide; nitrosureas such as Carmustine, Lomustine or Streptozocin; and inorganic metal complex agents such as Cisplatin, Carboplatin or Oxaliplatin;

plant alkaloids, e.g. taxanes (e.g., Docetaxel or Paclitaxel), vinca alkaloids (e.g., Vinblastine, Vincristine or Vinorelbine), camptothecan analogs (e.g., Irinotecan or Topotecan) and podophyllotoxins (e.g., Etoposide or Tenisopide);

antitumor antibiotics, e.g. anthracyclines, such as Daunorubicin, Doxorubicin, Epirubicin, Idarubicin, or Mitoxantrone; chromomycins, such as Dactinomycin or Plicamycin; and other antitumor antibiotics such as Bleomycin or Mitomycin;

antimetabolites, e.g. folic acid antagonists, such as Methotrexate; pyrimidine antagonists, such as Capecitabine, Cytarabine, 5-Fluorouracil (5-FU), Foxuridine or Gemcitabine; purine antagonists, such as 6-Mercaptopurine or 6-Thioguanine; adenosine deaminase inhibitors, such as Cladribine, Fludarabine, Nelarabine or Pentostatin; and ribonucleotide reductase inhibitors, such as Hydroxyurea;

topoisomerase inhibitors, e.g. topoisomerase I inhibitors, such as Ironotecan or Topotecan; and topoisomerase II inhibitors, such as Amsacrine, Etoposide, Etoposide Phosphate or Teniposide.

The PEGylated G-CSF polypeptides of the invention will be administered to patients in an "effective" or "therapeutically effective" dose, i.e. a dose that is sufficient to produced the desired effects in relation to the condition for which it is administered, in particular a dose that under the given conditions is sufficient to result in the desired stimulation of neutrophils. The exact dose may depend on factors such as the individual patient and the disorder being treated, and will be able to be determined by one skilled in the art, typically a medical doctor. The dosage of the PEGylated G-CSF polypeptide may e.g. be approximately the same order of magnitude as the current recommended dosage for pegfilgrastim (Neulasta®), which is 6 mg per adult patient. An appropriate dose of the PEGylated G-CSF polypeptide of the invention is therefore contemplated to be in the range of from about 1 mg to about 15 mg, such as from about 2 mg to about 15 mg, e.g. from about 3 mg to about 12 mg. A suitable dose may thus be, for example, about 3 mg, about 6 mg, or about 9 mg. In each case, the dosages are expressed as a standard dose per patient, where the patient is an adult or otherwise weighs at least 45 kg. Alternatively, the dosage may be determined according to the weight of the patient, such that an appropriate dose of the G-CSF polypeptide of the invention is in the range of from about 10 µg/kg to about 200 µg/kg, such as from about 25 µg/kg to about 150 µg/kg, e.g. from about 30 µg/kg to about 120 µg/kg. A suitable dose may thus be, for example, about 30 µg/kg, about 60 µg/kg, about 90 µg/kg or about 120 µg/kg.

The invention is further described by the following non-limiting examples.

EXAMPLES

Example 1

Preparation and Analysis of a Partially De-PEGylated G-CSF Variant

Sample Preparation and De-PEGylation

A G-CSF variant having the substitutions K16R, K34R, K40R, T105K and S159K compared to wild-type human G-CSF (SEQ ID NO:1) was produced from CHO-K1 cells substantially as described in WO 03/006501. 200 mL of 4.5 mg/mL of the G-CSF variant (900 mg G-CSF) was PEGylated using mPEG-SPA 5000 (Nektar Therapeutics). Briefly, 100 mL of a 13.2% (w/w) solution of mPEG-SPA 5000 was added over a period of 10 minutes to the 200 mL of G-CSF solution and gently stirred to ensure sufficient mixing. The sample was allowed to incubate for 44 minutes at 21±3° C., pH 8.5, with gentle stirring. The sample mixture was subsequently adjusted to pH 9.5 using a stock solution of 800 mM boric acid pH 10.0. The sample was then incubated at 21±3° C. for 24 hours without stirring. The sample was then diluted approx. 2.5 fold with 100 mmol/kg citric acid, 20 mmol/kg NaOH, pH 2.5, to a final pH of 3.5.

Isolation of Partially De-PEGylated G-CSF

After reduction of the pH to 3.5, the sample was loaded immediately onto a VL44 (Millipore) column packed with approx. 225 mL of SP-Sepharose HP (Amersham, GE Healthcare) equilibrated with 20 mmol/kg citric acid, 15 mmol/kg NaOH, pH 3.4. After loading of the material, the column was washed to remove unbound material such as free mPEG-acid. A linear gradient of 25-100% elution buffer (20 mmol/kg citric acid, 20 mmol/kg NaOH, 200 mmol/kg NaCl, pH 3.5) was used to elute the PEGylated G-CSF from the column. The gradient was developed for 25 CV (column volumes). The column step was performed at 21±3° C. and all buffers used were adjusted to the same temperature. The column load was 4.1 mg protein/ml resin and the flow was 8 CV/hour.

Fractions having a sample size of 40 mL were collected and analysed by SDS-PAGE. Based on the SDS-PAGE analysis a product pool of 1440 mL, corresponding to about 6.5 CV, containing isolated G-CSF having primarily 3 attached PEG groups per G-CSF molecule was made. It is contemplated that the volume of the product pool can be reduced by increasing the steepness of the elution gradient.

The product pool was diafiltered to approx. 200 mL and subsequently diafiltered into 10 mM sodium acetate, 43 mg/mL, pH 4.0 and concentrated to 4.9 mg/mL using a Millipore LabScale TFF-system equipped with two 50 cm² Millipore Pellicon XL membranes with a molecular weight cut-off (MWCO) of 30 kDa.

Results

The product pool was ultrafiltered and diafiltered into 10 mM Na-acetate, 43 mg/ml mannitol, pH 4.0 and subjected to physico-chemical characterization. FIG. 1 shows a scan of the SDS-PAGE analysis of the G-CSF variant that was PEGylated, partially de-PEGylated, and purified as described above, the seven lanes shown being as follows:

| | |
|---|---|
| 1 | Molecular weight marker |
| 2 | After PEGylation |
| 3 | pH 9.5, T = 0 h |
| 4 | pH 9.5, T = 24 h |
| 5 | Upon application on cation exchange column |
| 6 | Flow through from cation exchange |
| 7 | Purified product |

A single major band in lane 7 is observed, corresponding to the G-CSF variant carrying 3 mPEG-SPA 5000 groups per polypeptide molecule. In addition, a minor band corresponding to G-CSF carrying 4 mPEG-SPA 5000 groups is also seen in lane 7. If desired, optimization or adjustment of the purification procedure by methods generally known in the art will allow this minor band corresponding to 4 PEG groups to be reduced or substantially eliminated, although this will lead to a slight reduction of the yield depending on the degree of purity required.

The yield of this procedure was 450 mg of purified, partially de-PEGylated G-CSF carrying primarily 3 PEG groups per polypeptide molecule, corresponding to an overall yield of 50%.

19

Example 2

Preparation and Analysis of a Partially De-PEGylated G-CSF Variant

Sample Preparation, De-PEGylation and Purification

A G-CSF variant having the substitutions K16R, K34R, K40R, T105K and S159K compared to wild-type human G-CSF (SEQ ID NO:1) was produced from CHO-K1 cells and subsequently PEGylated using mPEG-SPA 5000 substantially as described in Example 1 above, resulting in 29 mL of 3.5 mg/mL PEGylated G-CSF variant. This was diafiltrated into 150 mM sodium borate, pH 9.5, using a Vivaspin filter device equipped with a 10 kDa MWCO filter. The final sample concentration was 4.7 mg/mL. The sample was then incubated at 21±3° C. for 42 hours.

After incubation, the sample was prepared for cation exchange chromatography by dilution with 30 mM citric acid, 10 mM NaOH, pH 2.9. The sample was then applied onto an XK 16/20 column (Amersham Biosciences) packed with 28 mL of SP-Sepharose HP resin. The column was equilibrated with an equilibration buffer of 20 mM citric acid, 15 mM NaCl, pH 3.5, prior to sample loading. After loading, the column was washed with the same buffer and eluted using a linear gradient of from 15 mM to 200 mM NaCl in 20 mM citric acid, pH 3.5, to separate the different PEGylated species.

Fractions were collected in tubes and analysed by SDS-PAGE analysis. A product pool containing the PEGylated G-CSF variant primarily containing 3 attached PEG moieties was made based on the SDS-PAGE. This product pool was diafiltrated and buffer exchanged using Vivaspin filter devices with a MWCO of 10 kDa. The sample was diafiltrated into 10 mM sodium succinate, 43 mg/mL, pH 4.0, and finally concentrated to 3.0 mg/mL.

Positional Isomer Analysis

Using cation exchange HPLC (CIEX-HPLC) combined with a sialidase pretreatment data was obtained on the composition of different positional PEG isomers in product pools containing multiple PEGylated species. In addition to heterogeneity after PEGylation due to the presence of different positional isomers, PEGylated G-CSF is also heterogeneous in that it contains one O-glycosylation site (Thr133) that can have zero, one or two sialic acid groups attached. In order to reduce the number of peaks in the chromatogram as a result of different numbers of sialic acid groups, a sialidase enzyme pre-treatment step is included prior to analysis. The sialidase treatment is performed by first diluting the G-CSF solution, if necessary, to 1 mg/ml with a 50 mM sodium acetate buffer, pH 5.0. after which 0.05 µl (0.25 mUnit) of sialidase is added per µg protein, and the sample is incubated at 37° C. for 18 hours to remove the sialic acids. The sample is then analysed the same day or kept at 4° C. until the day of analysis. HPLC was performed using a PolySULFOETHYL A™ cation exchange HPLC column (PolyLC Inc.), with UV detection at 214 nm. Characterization of the different peaks was performed by SDS-PAGE analysis after manual collection from the PolySULFOETHYL A™ CIEX column.

Results—PEG Loss

Figure 2:
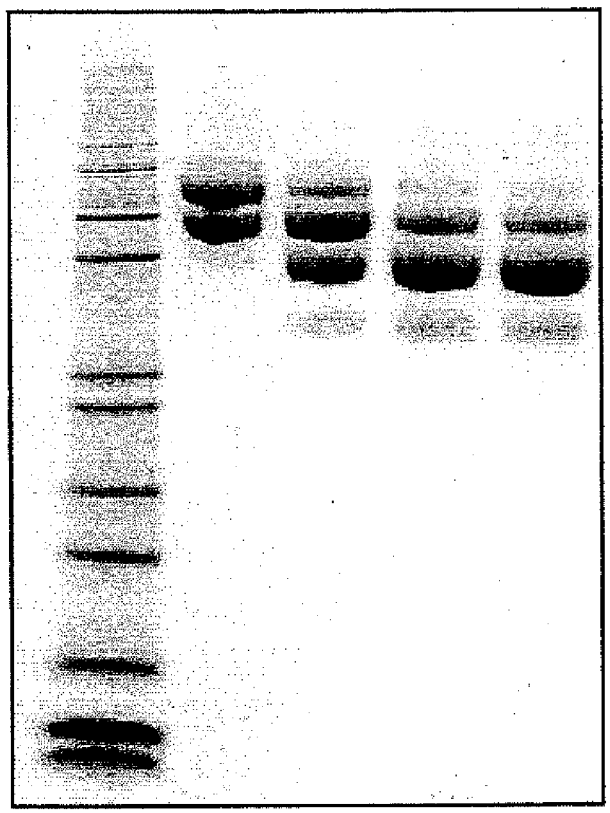
FIG. 2 shows a scan of an SDS-PAGE analysis of a G-CSF that was PEGylated and partially de-PEGylated as described herein.

The buffer-exchanged sample was analysed by SDS-PAGE to estimate the degree of PEG loss as a function of time. The results (see FIG. 2) were similar to those illustrated in FIG. 1 for Example 1, with only minimal changes in the overall degree of PEGylation being observed between samples incubated for 24 or 42 hours (FIG. 2, lanes 4 and 5).

20

Results—Assessment of Positional Isomers in Product Pools

Figure 3:
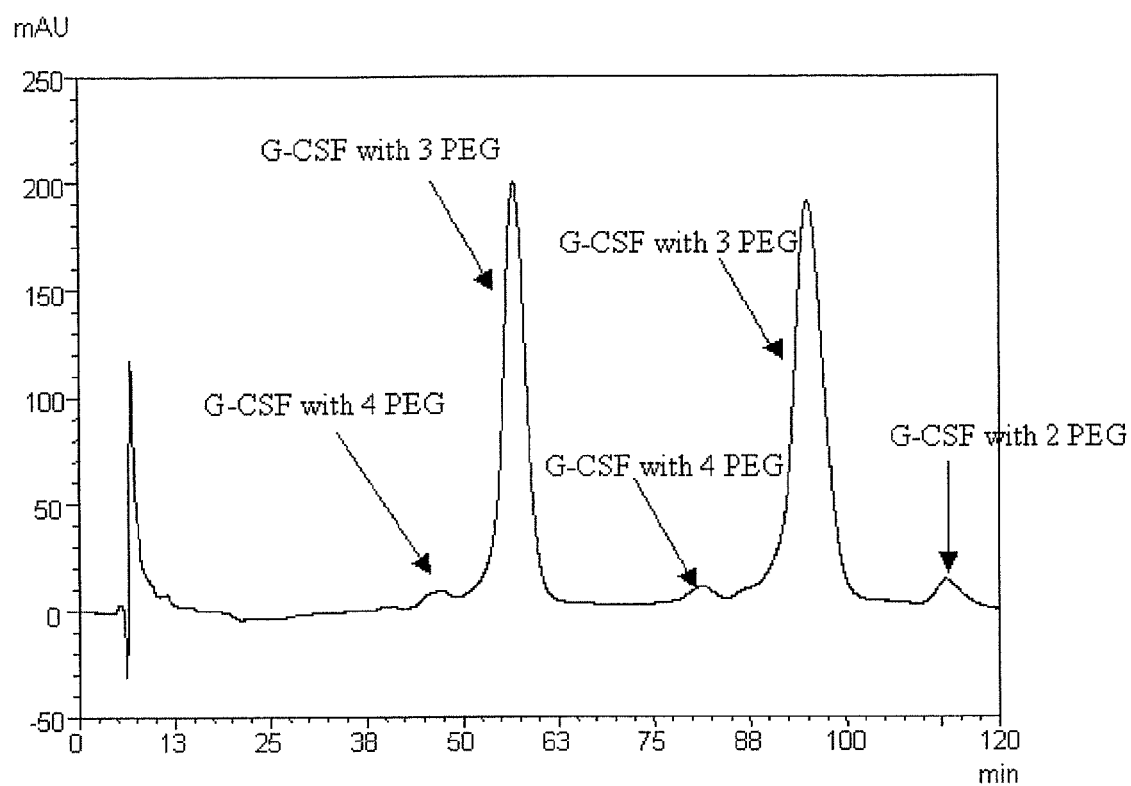
FIG. 3 shows a cation exchange chromatogram of a partially de-PEGylated product pool prepared according to the invention.

FIG. 3 shows a cation exchange chromatogram of the partially de-PEGylated product pool according to the invention obtained as described above containing primarily three PEG 5000 groups as judged by SDS-PAGE analysis. The two major peaks each represent one major positional isomer carrying three PEG 5000 groups. The three minor peaks represent two positional isomers carrying four PEG groups and one positional isomer carrying two PEG groups.

The two major peaks were collected and subjected to native peptide map analysis to determine the position of the attached PEG groups. It was found that the two major positional isomers are PEGylated on the following amino acid residues:

Isomer A: N-terminal, Lys23 and Lys159
Isomer B: N-terminal, Lys105 and Lys159

These two major isomers represented more than 95% of the positional isomers present in the sample.

Example 3

Comparative Example

Figure 4:
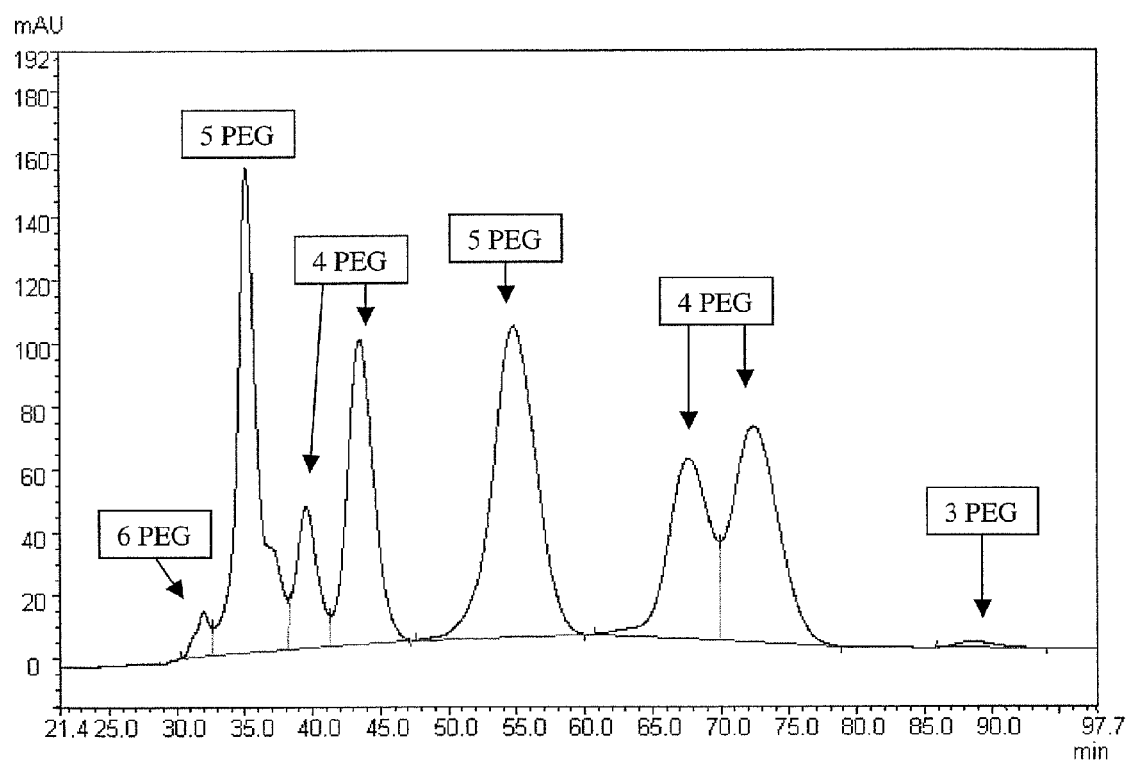
FIG. 4 shows a cation exchange chromatogram of a purified, PEGylated G-CSF variant that was not subject to de-PEGylation according to the invention.

For comparative purposes, FIG. 4 shows a cation exchange chromatogram of a purified, PEGylated G-CSF variant that was not subject to de-PEGylation according to the present invention. The G-CSF variant in this case had the same five substitutions compared to native human G-CSF as indicated above in Examples 1 and 2, i.e. K16R, K34R, K40R, T105K and S159K. It was prepared and PEGylated with mPEG-SPA 5000 substantially as described in Example 1, with the exception of the fact that it was not subjected to incubation at pH 9.5 for removal of labile PEG moieties. As a result, the PEGylated variant comprised a mixture of a number of different PEG isomers having 2-6 attached PEG moieties. This mixture of positional isomers was purified using cation exchange chromatography substantially as described in Example 1. A fraction containing primarily 4-5 attached PEG moieties was isolated and, after ultrafiltration and diafiltration substantially as described in Example 1, was subjected to CIEX-HPLC analysis as described above. This fraction corresponds to the 3-PEG fraction described in Examples 1 and 2, but with additional (labile) PEG groups being attached at one or two positions relative to the partially de-PEGylated 3-PEG product, i.e. the purified product in this case primarily contains 4-5 attached PEG groups.

Compared to the partially de-PEGylated product prepared according to the invention whose composition is shown in FIG. 3, the product shown in FIG. 4 is clearly a much more complex and heterogeneous mixture. Whereas the product prepared according to the invention shown in FIG. 3 contains more than 95% of the two major positional isomers each having 3 PEG moieties, the product shown in FIG. 4 comprises six major positional isomers each having either 4 or 5 attached PEG moieties. These six 4-5 PEG positional isomers comprise labile PEG moieties at one or both of Ser66 or Tyr165 (data not shown), as well as stable PEG moieties at the N-terminal and at 1 or 2 of positions K23, K105 and K159. Due to steric hindrance, not all of these positions on a single G-CSF polypeptide can be occupied by PEG moieties. The product shown in FIG. 4 thus contains a heterogeneous mixture of the six following major PEG isomers:

N-terminal, K23, S66, K159, Y165 (5-PEG)
N-terminal, S66, K105, K159, Y165 (5-PEG)
N-terminal, K23, S66, K159 (4-PEG)
N-terminal, K23, S66, Y165 (4-PEG)
N-terminal, S66, K105, K159 (4-PEG)
N-terminal, S66, K105, Y165 (4-PEG)

Example 4

Stability Data

The stability of the attached PEG moieties was tested in 5 different aqueous formulations stored at four different temperatures. The polypeptide was a G-CSF variant having the five substitutions listed in Example 1 and which was prepared, PEGylated, and subject to partial de-PEGylation and then purified also as described in Example 1. The formulations tested were as follows:

|  | Units | Formulation A | B | C | D |
|---|---|---|---|---|---|
| G-CSF | mg/ml | 2 | 10 | 2 | 2 |
| Na-Acetate | mM | 10 | 10 | 10 | 10 |
| Tween ®80 | mg/ml | — | — | 0.05 | — |
| Tween ®20 | mg/ml | — | — | — | 0.05 |
| Mannitol | mg/ml | 43 | 43 | 43 | 43 |

The pH of each of the formulations was 4.0.

Using CIEX-HPLC, the distribution of PEG isomers in each sample was determined after 26 days, 56 days and 89 days to investigate the stability of the PEGylation. The results are shown in the table below.

| Formulation | Temp. | Day | 3 PEG | Others/not characterized | 2 PEG |
|---|---|---|---|---|---|
| A | — | 0 | 92.3 | 7.8 | 0 |
|  | −80° C. | 26 | 93.3 | 6.6 | 0 |
|  | 5° C. |  | 93.5 | 6.4 | 0.1 |
|  | 25° C. |  | 94.1 | 5.5 | 0.3 |
|  | 35° C. |  | 94.3 | 4.7 | 0.8 |
|  | −80° C. | 56 | 95.4 | 4.7 | 0 |
|  | 5° C. |  | 95.3 | 4.7 | 0 |
|  | 25° C. |  | 95.3 | 3.8 | 0.9 |
|  | 35° C. |  | 95.3 | 3.0 | 1.7 |
|  | −80° C. | 89 | 96.1 | 3.9 | 0 |
|  | 5° C. |  | 95.9 | 4.1 | 0 |
|  | 25° C. |  | 96.1 | 3.1 | 0.8 |
|  | 35° C. |  | 95.5 | 2.7 | 1.8 |
| B | — | 0 | 92.4 | 7.6 | 0 |
|  | −80° C. | 26 | 93.5 | 6.5 | 0.0 |
|  | 5° C. |  | 93.4 | 6.5 | 0.1 |
|  | 25° C. |  | 94.0 | 5.7 | 0.3 |
|  | 35° C. |  | 94.2 | 5.0 | 0.8 |
|  | −80° C. | 56 | 95.1 | 4.9 | 0 |
|  | 5° C. |  | 95.4 | 4.7 | 0 |
|  | 25° C. |  | 95.2 | 4.3 | 0.6 |
|  | 35° C. |  | 96.2 | 2.4 | 1.4 |
|  | −80° C. | 89 | 95.9 | 4.1 | 0 |
|  | 5° C. |  | 95.9 | 4.1 | 0 |
|  | 25° C. |  | 96.8 | 3.2 | 0 |
|  | 35° C. |  | 95.5 | 2.6 | 1.9 |
| C | — | 0 | 92.1 | 7.9 | 0 |
|  | −80° C. | 26 | 93.8 | 6.1 | 0 |
|  | 5° C. |  | 94.1 | 5.8 | 0 |
|  | 25° C. |  | 94.0 | 5.7 | 0.3 |
|  | 35° C. |  | 94.6 | 4.5 | 0.8 |
|  | −80° C. | 56 | 95.1 | 4.9 | 0 |
|  | 5° C. |  | 95.1 | 4.9 | 0 |
|  | 25° C. |  | 94.1 | 4.8 | 1.1 |
|  | 35° C. |  | 95.1 | 3.0 | 1.9 |
|  | −80° C. | 89 | 95.9 | 4.1 | 0 |
|  | 5° C. |  | 95.9 | 4.1 | 0 |
|  | 25° C. |  | 96.1 | 3.2 | 0.7 |
|  | 35° C. |  | 95.5 | 2.7 | 1.8 |
| D | — | 0 | 92.6 | 7.5 | 0 |
|  | −80° C. | 26 | 93.8 | 6.1 | 0.1 |
|  | 5° C. |  | 93.6 | 6.3 | 0.1 |
|  | 25° C. |  | 93.7 | 6.1 | 0.3 |
|  | 35° C. |  | 94.4 | 4.9 | 0.8 |
|  | −80° C. | 56 | 95.3 | 4.7 | 0 |
|  | 5° C. |  | 95.2 | 4.8 | 0 |
|  | 25° C. |  | 95.2 | 4.0 | 0.8 |
|  | 35° C. |  | 95.5 | 3.3 | 1.3 |
|  | −80° C. | 89 | 96.0 | 4.0 | 0 |
|  | 5° C. |  | 96.0 | 4.0 | 0 |
|  | 25° C. |  | 96.2 | 3.1 | 0.7 |
|  | 35° C. |  | 95.7 | 2.5 | 1.8 |

The above results show that regardless of the formulation and the storage temperature, the PEGylation is highly stable, with the proportion of 3 PEG isoforms being very close to 95% at all temperatures when sampled at either 26, 56 or 89 days. The only difference readily seen from the table is a slight decrease over time, using the −80° C. data as a reference, in the proportion of the other/non-characterized forms, mainly for samples stored at 25° C. or 35° C., and a corresponding increase in the proportion of 2 PEG isomers for these samples.

By comparison, the table below shows similar data, determined after 20 and 83 days of storage, for the same G-CSF variant in a formulation similar to those described above, but prepared without the de-PEGylation step of the present invention, i.e. corresponding to the product described in comparative Example 3 above. The formulation in this case had a pH of 4.0 and consisted of 15 mM sodium acetate, 45 mg/ml mannitol, and 5 mg/ml of the PEGylated G-CSF variant, which at the beginning of the experiment contained primarily (98-99%) 4-5 attached PEG moieties. The table below shows the distribution of the PEG isoforms as determined after 83 days at the four temperatures indicated as well as after 20 days at two of these temperatures. It is seen that the proportion of the G-CSF polypeptides containing 4-5 PEG moieties decreases just slightly after 83 days when stored at 5° C., while there is a substantial loss of 4-5 PEG isoforms and a corresponding increase in 3 PEG isoforms when stored at 25° C., and a far greater loss of 4-5 PEG isoforms and corresponding increase in 3 PEG isoforms at 35° C. This illustrates that in the absence of the de-PEGylation method of the present invention, a PEGylated G-CSF polypeptide prepared as described above contains labile PEG groups that over time and depending on the temperature will be detached from the polypeptide when stored in an aqueous formulation.

| Temp. | Day | 4-5 PEG | 3 PEG | Others/not characterized |
|---|---|---|---|---|
| — | 0 | 98.6% | 0 | 1.4% |
| −80° C. | 20 | 98.1% | 0.5% | 1.4% |
| 35° C. |  | 96.0% | 2.9% | 1.1% |
| −80° C. | 83 | 97.9% | 0.6% | 1.6% |
| 5° C. |  | 97.6% | 1.0% | 1.5% |
| 25° C. |  | 90.6% | 8.4% | 1.1% |
| 35° C. |  | 78.1% | 21.5% | 0.5% |

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. All publications, patents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

SBA), or mPEG-succinimidyl α-methylbutanoate (mPEG-SMB) under conditions to produce a plurality of positional PEG isomers of the recombinant G-CSF polypeptide.

d) reacting the plurality of positional PEG isomers at a pH of 8.5 to 10.5 under conditions which produce a plurality of partially dePEGylated lysine/N-terminal positional PEG isomers of the recombinant G-CSF polypeptide, wherein at least 80% of the plurality of the partially de PEGylated lysine/N-terminal positional PEG isomers are a mixture of two positional PEG isomers each having three PEG groups, wherein one of the two positional

The invention claimed is:

1. A plurality of partially dePEGylated lysine/N-terminal positional PEG isomers of a recombinant G-CSF polypeptide, said recombinant G-CSF polypeptide comprising the substitutions K16R, K34R, K40R, T105K and S159K relative to wild-type human G-CSF, produced by a method comprising:
   a) expressing the recombinant G-CSE polypeptide in a host cell;
   b) isolating the recombinant G-CSF polypeptide;
   c) reacting the isolated recombinant G-CSF polypeptide with an amine-specific activated PEG selected from the group consisting of mPEG-succinimidyl propionate (mPEG-SPA), mPEG-succinimidyl butanoate (mPEG- PEG isomers has PEG moieties attached the N-terminal, Lys23 and Lys159 and the other of the two positional PEG isomers has PEG moieties attached at the N-terminal, Lys105 and Lys159.

2. A substantially purified mixture of lysine/N-terminal positional PEG isomers of a recombinant G-CSF polypeptide, said recombinant G-CSF polypeptide comprising the substitutions K16R, K34R, K40R, T105K and S159K relative to wild-type human G-CSF, produced by a method comprising:
   a) expressing the recombinant G-CSF polypeptide in a host cell;
   b) isolating the recombinant G-CSF polypeptide;

c) reacting the isolated recombinant G-CSF polypeptide with an amine-specific activated PEG selected from the group consisting of mPEG-succinimidyl propionate (mPEG-SPA), mPEG-succinimidyl butanoate (mPEG-SBA), or mPEG-succinimidyl α-methylbutanoate (mPEG-SMB) to produce a plurality of positional PEG isomers of the recombinant G-CSF polypeptide;

d) reacting the plurality of positional PEG isomers at a pH of 8.5 to 10.5 under conditions producing a plurality of partially dePEGylated lysine/N-terminal positional PEG isomers of the recombinant G-CSF polypeptide, wherein at least 80% of the plurality of partially dePEGylated lysine/N-terminal positional PEG isomers are a mixture of two positional PEG isomers each having three PEG groups, wherein one of the two positional PEG isomers has PEG moieties attached the N-terminal, Lys23 and Lys159 and the other of the two positional PEG isomers has PEG moieties attached at the N-terminal, Lys105 and Lys159; and e) subjecting the plurality of lysine/N-terminal positional PEG isomers of the recombinant G-CSF polypeptide produced in step d) to one or more chromatographic purification steps, thereby producing a substantially purified mixture of lysine/N-terminal positional PEG isomers of the G-CSF polypeptide.

3. A pharmaceutical composition comprising a substantially purified mixture of lysine/N-terminal positional PEG isomers of a recombinant G-CSF polypeptide, said recombinant G-CSF polypeptide comprising the substitutions K16R, K34R, K40R, T105K and S159K relative to wild-type human G-CSF, produced by a method comprising:

a) expressing the recombinant G-CSF polypeptide in a host cell;

b) isolating the recombinant G-CSF polypeptide;

c) reacting the isolated recombinant G-CSF polypeptide with an amine-specific activated PEG selected from the group consisting of mPEG-succinimidyl propionate (mPEG-SPA), mPEG-succinimidyl butanoate (mPEG-SBA), or mPEG-succinimidyl α-methylbutanoate (mPEG-SMB) to produce a plurality of positional PEG isomers of the recombinant G-CSF polypeptide;

d) reacting the plurality of positional PEG isomers at a pH of 8.5 to 10.5 to produce a plurality of partially dePEGylated lysine/N-terminal positional PEG isomers of the recombinant G-CSF polypeptide, wherein at least 80% of the plurality of the partially de PEGylated lysine/N-terminal positional PEG isomers are a mixture of two positional PEG isomers each having three PEG groups; wherein one of the two positional PEG isomers has PEG moieties attached the N-terminal, Lys23 and Lys159 and the other of the two positional PEG isomers has PEG moieties attached at the N-terminal, Lys105 and Lys159 e) subjecting the plurality of lysine/N-terminal positional PEG isomers of the recombinant G-CSF polypeptide produced in step d) to one or more chromatographic purification steps, thereby producing a substantially purified mixture of lysine/N-terminal positional PEG isomers of the G-CSF polypeptide; and f) combining an effective dose of the substantially purified mixture of lysine/N-terminal positional PEG isomers of the recombinant G-CSF polypeptide with at least one pharmaceutically acceptable excipient to produce a pharmaceutical composition.

4. The plurality of partially dePEGylated lysine/N-terminal positional PEG isomers of claim 1, wherein the amine-specific activated PEG is mPEG-SPA with a molecular weight of about 5 kDa.

5. The substantially purified mixture of lysine/N-terminal positional PEG isomers of claim 2, wherein the amine-specific activated PEG is mPEG-SPA with a molecular weight of about 5 kDa.

6. The pharmaceutical composition of claim 3, wherein the amine-specific activated PEG is mPEG-SPA with a molecular weight of about 5 kDa.

* * * * *